United States Patent [19]

Eaton

[11] Patent Number: 4,548,927

[45] Date of Patent: Oct. 22, 1985

[54] METHOD AND AGENTS FOR RAISING ANIMAL TOLERANCE TO OXIDANT STRESS-INDUCING ANTIBIOTICS

[76] Inventor: John W. Eaton, 1804 Irving Ave. South, Minneapolis, Minn. 55403

[21] Appl. No.: 497,786

[22] Filed: May 25, 1983

[51] Int. Cl.$^4$ ............................................. A61K 31/71
[52] U.S. Cl. ........................................ 514/34; 514/222; 514/223
[58] Field of Search ........................ 424/180, 181, 247

[56] References Cited

U.S. PATENT DOCUMENTS

| | | | |
|---|---|---|---|
| 3,590,028 | 6/1971 | Arcamone | 424/180 |
| 3,876,783 | 4/1975 | Gavrilescu et al. | 424/313 |
| 4,170,640 | 10/1979 | Grigg et al. | 424/177 |
| 4,225,588 | 9/1980 | Grigg et al. | 424/177 |

FOREIGN PATENT DOCUMENTS 2817289 10/1978 Fed. Rep. of Germany .

OTHER PUBLICATIONS

Chemical Abstracts; vol. 88, (1978), Burrows et al., 1106t.
Chemical Abstracts; vol. 92, (1980), Burrows, 35307g.
Merck Index; 8th Edition (1968); "Methylene Blue".
G. W. Grigg et al., "Amplification of Phleomycin and Bleomycin-Induced Antibiotic Activity in E. Coli etc.", Jour. Antibiotics, vol. XXX, No. 10, pp. 870–888, (Oct. 1977).
A. D. Wolfe et al., "Labilizing Action of Intercalating Drugs and Dyes on Bacterial Ribosomes", Biochemistry, vol. 11, No. 9, pp. 1549–1572, Table I, (Apr. 25, 1972).
W. Krivit, "Hematological Aspects of Vitamin E Adriamycin Cardiotoxicity Amelioration by α-Tocopherol", Chemical Abstracts, vol. 93, No. 5, p. 1, Abstract No. 36500x (Aug. 4, 1980).

*Primary Examiner*—Leonard Schenkman
*Assistant Examiner*—Joseph A. Lipovsky
*Attorney, Agent, or Firm*—David A. Jackson; Daniel H. Bobis

[57] ABSTRACT

A method and agents are disclosed for raising the tolerance of animal tissue to antibiotic compounds that induce oxidant stress. The method comprises administering one or more nontoxic redox compounds to the locus of administration of the antibiotic in an amount sufficient to diminish the production of the potentially toxic oxidants. The redox compounds may be administered by various parenteral techniques. The agents comprise redox compounds and include redox dyes such as those of the thiazine group. Of this group methylene blue is preferred. A method for treating cancer in animals is also disclosed.

29 Claims, 4 Drawing Figures

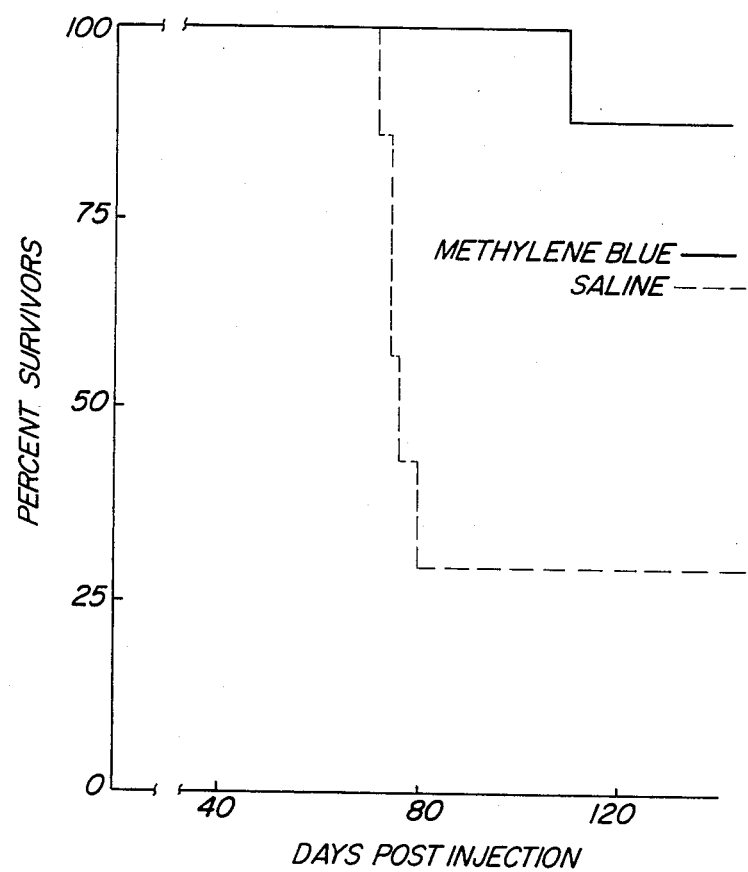

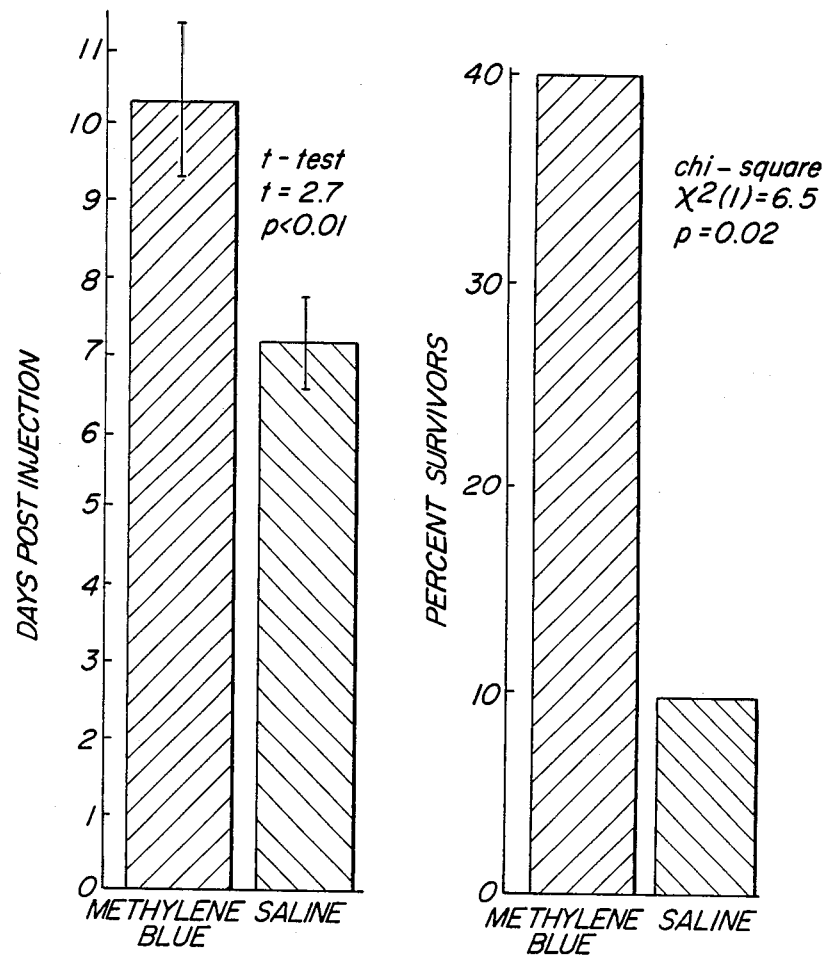

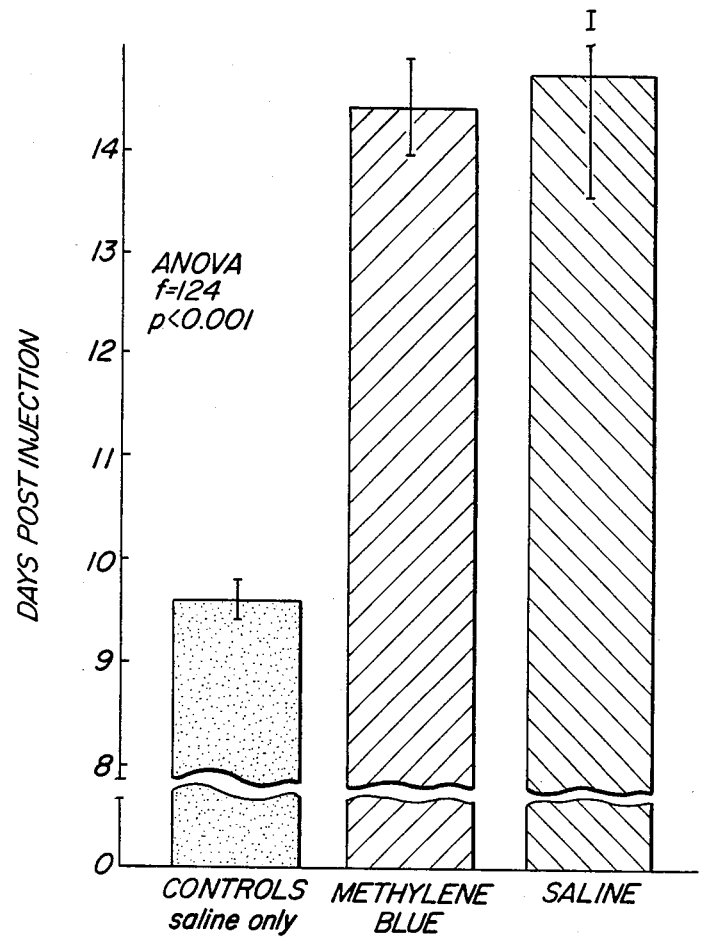

METHOD AND AGENTS FOR RAISING ANIMAL TOLERANCE TO OXIDANT STRESS-INDUCING ANTIBIOTICS

BACKGROUND OF THE INVENTION

1. Field of the Invention

The present invention relates generally to the administration of certain antibiotics to animals, and in particular to antibiotics that induce oxidant stress, and are consequently dose-limited.

2. Description of the Prior Art

Numerous agents have been developed, tested and utilized in the treatment of various cancers by chemical means. Thus, a number of effective anti-cancer agents have been isolated which offer sufficient antineoplastic activity to warrant their use in cancer chemotherapy. A particularly effective family of agents belongs to the anthracycline group, and includes daunorubicin, doxorubicin, Chromomycin A, olivomycin, Rhodomycin A and Rhodomycin B. Another effective antineoplastic is the glycopeptide antibiotic, bleomycin.

While the above representative antibiotics have proven effective, they possess a serious limitation to their use, as there is an absolute, cumulative dose limitation to their administration that is believed to result from their participation in the generation of toxic levels of oxidants. For example, it has been found that amounts of doxorubicin and other anthracyclines administered beyond the dose-limiting level, causes cumulative damage to myocardial cells, that leads to serious and often lethal congestive cardiomyopathy. Regrettably, the maximum amount of these compounds that can be administered before cardiotoxicity results, is frequently inadequate to achieve even minor arrest of certain cancerous conditions. The mechanism of participation by the antibiotics of the anthracycline group in causing cardiotoxicity, is believed to be due to the reduction of the anthracycline and the subsequent reaction of the reduced form with oxygen to form toxic metabolites believed to be free radical species, all in quantities which exceed the capacity of the endogenous myocytic detoxification pathways.

In particular, doxorubicin causes the production of free radicals from NADPH (reduced nicotinamide adenine dinucleotide phosphate) and NADH (reduced nicotinamide adenine dinucleotide) present in microsomal systems, increases oxygen consumption of both hepatic microsomes and heart sarcosomes, and stimulates superoxide formation in cardiac submitochondrial particles, with the result that oxygen radical levels exceed the disposing capacity of the cells. See Handa, K., and S. Santo. "Generation of Free Radicals of Quinone Containing Anticancer Chemicals in NADPH-Microsome Systems as Evidenced by Initiation of Sulfite Oxidation," *JAPAN S. CANCER RES.* (Tokyo). 66:43–47 (1975); Bachur, N. R., Gordon, S. L., and M. V. Gee. "A General Mechanism for Microsomal Activation of Quinone Anticancer Agents to Free Radicals," *CANCER RES.* 38:43–47 (1978); Goodman, J., and P. Hochstein. "Generation of Free Radicals and Lipid Peroxidations by Redox Cycling of Andriamycin and Daunomycin," *BIOPHYSICAL RES. COMMUNICATIONS.* 77(#2) (1977); Thayer, W. S. "Andriamycin Stimulated Superoxide Formation in Submitochondrial Particles," *CHEM.-BIOL. INTERACT.* 19:265–278 (1977); Meyers, C. E., McGuire, W., and R. Young. "Andriamycin: Amelioration of Toxicity by Alpha Tocopherol," *CANCER TREAT. REP.* 60:961–926 (1976) and Doroshow, J. "Role of NADH Dehydrogenase in Oxygen Radical Formation by Anthracycline (a) Antibiotics," *PROC. AM. ASSOC. CLIN. RES.* 23:172 (1982).

In view of the above, various methods have been investigated and developed that attempt to prevent this antibiotic-induced free radical-mediated damage to normal tissues, however these techniques have all been of limited success in humans ("In International Symposium on Andriamycin", S. K. Carter, A. DiMarco, M. Ghione, et. al., editors, Springer-Verlag, New York. (1972)). Thus, Vitamin E has been used with some effect in certain species, but has failed to work at tolerable doses in humans (Krivit, W., "Adriamycin Cardiotoxicity Amelioration α-tocopherol", *AM. J. PED. HEMATOL./ONCOL.* 1(#2):151–153 (1979); and Wang, Y. M., Madanat, D. D., Kimball, T. C., Gleiser, C. A., Ali, M., Kaufman, W., and Vaneys, J., "Effect of Vitamin E Against Adriamycin Induced Toxicity in Rabbit", *CANCER RES.* 40:1022–27 (1980).

Co-enzymes $Q_9$ and $Q_{10}$ are of potential utility but have thus far offered no proven clinical benefit ("In The Biomedical and Clinical Aspects of Coenzyme Q, Vol. I", K. Folkers, and Y. Yamamura, editors, Elsevier Scientific Publishing Company, New York. (1977); "In The Biomedical and Clinical Aspects of Coenzyme Q, Vol. II", Y. Yamamura, K. Folkers, and Y. Ito, editors, Elsevier/North Holland Biomedical Press, New York. (1980); and "In The Biomedical and Clinical Aspects of Coenzyme Q, Vol. III", K. Folkers, and Y. Yamamura, editors, Elsevier/North-Holland Biomedical Press, New York (1981)).

Lastly, N-acetyl cysteine and other sulfhydryl group-donating compounds have shown mixed results, in that they have often protected the tumor cells as well as the normal host tissues from this antibiotic-induced damage (Doroshow, J., Locker, G. Y., Ifrim, I., and Myers, C. E., "Prevention of Doxorubicin Cardiac Toxicity in the Mouse by N-Acetylcysteine." *J. CLINIC. INVEST.* 68:1053–1064 (1981)).

The foregoing lack of conclusive efficacy, coupled with the apparent lack of discrimination (indicated with respect to the sulfhydryl group-donating compounds) suggests that a great need continues to exist for the development of a specific and efficacious method for the control of antibiotic-induced oxidant stress and consequent toxicity, with the concurrent benefit of the increased tolerance to the above discussed anti-cancer agents.

SUMMARY OF THE INVENTION

In accordance with the present invention a method is disclosed for increasing animal tolerance to antibiotics that induce oxidant stress. The method comprises administering an effective amount of a nontoxic redox agent to the animal. The redox agent may comprise an appropriate redox dye that can be administered either directly to the tissues to which the oxidant stress-inducing antibiotic is administered, or indirectly by either oral or parenteral routes. In the instance of parenteral administration, one may introduce the redox agent intraperitoneally, as well as intravenously and even subcutaneously. The redox agent may be administered either before or concurrently with the administration of the antibiotic. Administration of the redox agent may also begin shortly after the commencement of the administration of the antibiotic. For example, the administration of the redox agent may commence within 5 to 30 minutes either before or after antibiotic administration begins. Further, while the exact effective quantities of redox agent will vary, particularly in relation to the amount of antibiotic administered, it may be administered in an amount of from about 25 mg/kg to about 300 mg/kg of animal body weight.

Suitable redox agents include redox dyes of the thiazine group. Exemplary redox dyes comprise methylene blue, thionin, Azure A, Azure B, Azure C, methylene green, new methylene blue N, toluidine blue O and methylene violet. A preferred redox dye is methylene blue.

The antibiotics of present interest are those that exhibit anti-neoplastic activity, and include antibiotics of the anthracycline group such as doxorubicin, daunorubicin, Chromomycin A, olivomycin, Rhodomycin A and Rhodomycin B; and the glycopeptide, bleomycin, which shows activity in the treatment of various cancers, including carcinomas and lymphomas.

The present invention also includes the redox agents that limit the free radical producing activity of oxidant stress-inducing antibiotics, and comprises those nontoxic redox dyes mentioned above. A further aspect of the present invention comprises a method for the treatment of cancerous tissues in animals, that comprises the administration to the animal of one of the above listed antibiotics and the nontoxic redox agent, the redox agent administered in an amount effective to reduce the free radical mediated damage of normal tissue attributable to the particular antibiotic.

The method and associated agents of the present invention are distinctive in that they operate with improved uniform efficacy and specificity, as they do not interfere with the anti-neoplastic activity of the antibiotics. Thus, the antibiotics may enter the tumorous cells and function in their characteristic manner without inhibition from the redox agents, and the redox agents do not appear to enter such cells. In such manner, therefore, the tumorous cells are attacked and killed, while the external, normal cells are protected.

Accordingly, it is a principal object of the present invention to provide a method for reducing the cardiotoxicity of oxidant stress-inducing antibiotic cancer treatment compounds.

It is a further object of the present invention to provide a method as aforesaid that facilitates an increase in the maximum dosage that the animal can receive of the said antibiotic compounds.

It is a still further object of the present invention to provide a method as aforesaid that is uniformly effective but does not reduce the anti-neoplastic activity of the said antibiotic compounds.

It is a still further object of the present invention to provide agents for administration in the method as aforesaid which are inexpensive and nontoxic.

It is a still further object of the present invention to provide a method for the treatment of cancer which utilizes the method and agents as aforesaid in conjunction with the said antibiotic compounds.

Other objects and advantages will become apparent to those skilled in the art from a review of the ensuing description which proceeds with reference to the following illustrative drawings.

BRIEF DESCRIPTION OF THE DRAWINGS

FIG. 2 graphically represents a comparison of animal mortality following comparative in vivo testing of the method and agents of the present invention, and a saline control.

FIG. 3 is a bar graph depicting the improvement in the survival rate of laboratory animals treated with a combination of doxorubicin and methylene blue, over animals treated with a mixture of doxorubicin and saline.

FIG. 4 graphically represents a comparison of the effect of the redox agent methylene blue on doxorubicin efficacy as measured by animal survivial.

DETAILED DESCRIPTION

Figure 1:
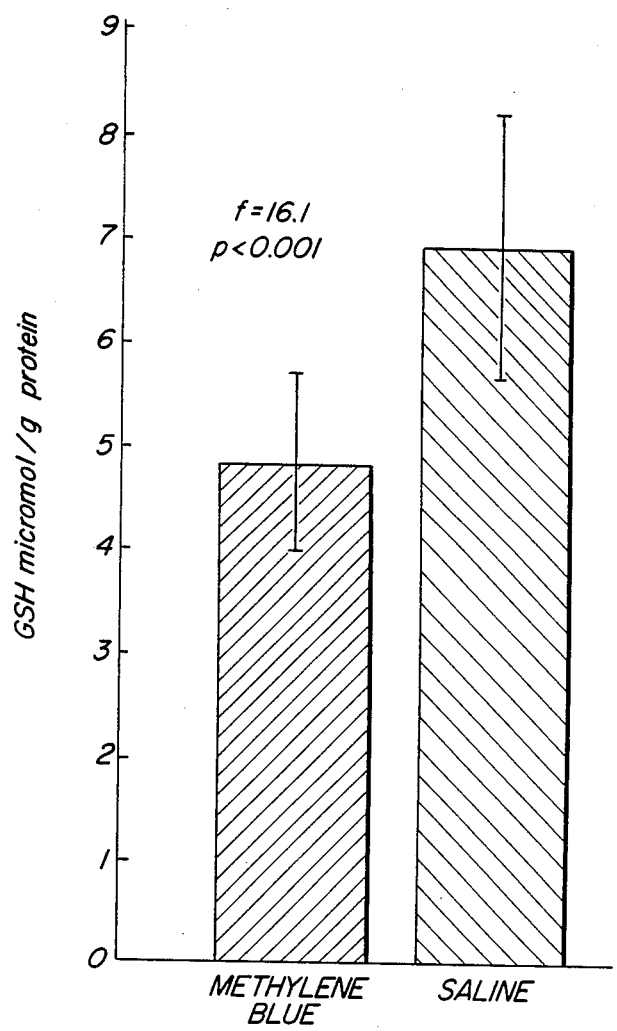
FIG. 1 graphically represents the effects on cardiac glutathione levels in control animals and animals injected with the agent and in accordance with the method of the present invention.

In accordance with the present invention, a method and corresponding agents are disclosed for raising the tolerance of animal tissue to antibiotic compounds that induce oxidant stress. The method in its simpliest aspect, comprises the administration of an effective of amount of one or more nontoxic redox agents, such as the redox dyes enumerated earlier herein.

As discussed previously, the dose limiting side effects of the antibiotic compounds of interest herein are believed to be attributable to the interaction between the antibiotic compounds and NADPH or NADH (Nicotinamide-Adenine Dinucleotide Phosphate and Nicotinamide-Adenine Dinucleotide respectively) or with their reducing proteins, with the result that the antibiotic compounds participate in the generation of free radical by-products in quantities that exceed the capacity of endogenous myocytic detoxification pathways (Meyer, C. D. McGuire, W. P., Liss, R. H. Ifrim, I., Grotzinger, K., and Young, R. C., "Adriamycin: The Role of Lipid Peroxidation in Cardiac Toxicity and Tumor Response", SCIENCE (Washington, D.C.). 197:165-67 (1977)).

The present inventor has likewise reasoned that the reduction of the oxidant stress-inducing antibiotics may be promoted by interaction with either NADH or NADPH, or their reducing proteins. In particular, examination of tissues subsequent to the administration of the oxidant stress-inducing antibiotic doxorubicin reveals some complexation between doxorubicin and certain cellular proteins that are present in the vicinity of the situs of the oxidation and resulting depletion of NADPH. It is therefore possible that the oxidation of NADH or NADPH may occur indirectly by the interaction of the antibiotic with these reducing proteins acting as mediators, either in addition to or in place of a direct interaction between the antibiotic and NADH or NADPH alone.

Regardless of the exact mechanism involved, it appears with respect to anthracycline antibiotics that the general interaction reflected by the oxidation of NADPH when the anthracycline antibiotic is in its vicinity is causally related to anthracycline cardiotoxicity, and that an interruption or interference with this interaction might facilitate at least a partial lifting of the dose limitation that attends the administration of anthracycline antibiotic compounds. To this end, the present invention proposes to administer to the locus of administration of the oxidant stress-inducing antibiotic, a compound which will interact with cell proteins, and is likewise capable of being chemically reduced by either NADH or NADPH and will thereby be capable of competing with these antibiotic compounds and to the extent that it is successful, preventing the production of toxic levels of oxidants.

Accordingly, it has been determined that certain nontoxic redox agents, such as suitable dyes may be so administered to the vicinity of antibiotic treatment, in amounts effective to successfully compete with the antibiotic for NADPH or its reducing proteins, and to thereby prevent the reduction of the antibiotic compound and subsequent cell destruction.

Suitable redox dyes include redox dyes of the thiazine group. These compounds are also identified as having Color Index numbers within the 52000 Series (those dyes having assigned numbers from 52000 to 52999). Particular members of this group include methylene blue, thionin, Azure A, Azure B, Azure C, methylene green, new methylene blue N, toluidine blue O and methylene violet. (See, COLOUR INDEX, 3rd Ed., Society of Dyers & Colourists, Publishers, London. 4:4469-4473 (1971). Preferably, methylene blue may be utilized.

Methylene blue is also known as methylthionine chloride and possesses the formula $C_{16}H_{18}ClN_3S$. It is soluble in water, alcohol and chloroform and insoluble in ether, and forms double salts with many inorganic salts. It has a broad scope of utility ranging from its use as a stain in bacteriology, and as a reagent for several chemicals and in mixed indicators, as well as its capability as an oxidation-reduction indicator. It has certain medicinal and therapeutic utilities, among them that it is routinely administered locally to aid in the detection of fistulae of the urogenital tract and of ruptured amniotic membranes in pregnant women. Methylene blue is also administered to patients suffering from methemoglobinemia as it is reduced within the red blood cell by an NADPH-dependent process to the leuko form of the dye, which in turn reduces methemoglobin (See "Physician's Desk Reference, Ed. 36" Medical Economics Company, Inc., Oradell, N.J., (1972)).

The antibiotic compounds that are the subject of the present method and associated agents, include antibiotics of the anthracycline group, such as compounds doxorubicin, daunorubicin, Chromomycin A, olivomycin, Rhodomycin A, and Rhodomycin B; and the glycopeptide antibiotic, bleomycin. These compounds have all proved effective in the treatment of various cancers, however are all cumulatively dose limited by virtue of their reduction by either NADH or NADPH or their reaction with their corresponding reducing proteins, and the consequent toxic activity of the resulting metabolites, as discussed in detail above. The tests presented hereinafter have been conducted with doxorubicin, as it is fairly representative of the antibiotic compounds relevant to this invention.

Doxorubicin is also known as 14-hydroxydaunomycin, and is also known by the trade name of Adriamycin. Its chemical formula is $C_{27}H_{29}NO_{11}$, and it has a molecular weight of 543.54. It is isolated from cultures of a mutant Streptomyces peucetius, called Streptomyces peucetius var caesius. Its isolation and preparation are set forth in U.S. Pat. No. 3,590,028, the disclosure of which is incorporated herein by reference. It is soluble in water, methanol and other aqueous alcohols but is practically insoluble in acetone, benzene, chloroform, ethyl ether and petroleum ether.

The present method contemplates the administration of the nontoxic redox agents by conventional means to place the agents to the extent possible, at the locus of oxidant generation. Thus, a variety of suitable administrative techniques may be utilized, preferably among them those that are oral as well as parenteral; examples of parenteral techniques include subcutaneous, intravenous and intraperitoneal injections, catheterizations, etc. Preferably with respect to the anthracycline antibiotics, the redox agent is administered in cyclic fashion to achieve continuous competitive oxidation of NADPH during the period of antibiotic administration, so that administration of the respective compounds may be concurrent. Alternately, administration of the redox agent may commence either shortly before or after the administration of the antibiotic has been initiated. Preferably, but by way of example only, administration of the redox agent may begin either 5 to 30 minutes before or after the administration of the antibiotic has been started. The exact time sequence and interval, however, may vary.

The dosage of the nontoxic redox agent may likewise vary, in general relation to the amount of the antibiotic being administered. In accordance with one embodiment of the invention, the redox agent may be administered within a range of from about 25 mg/kg to about 300 mg/kg based on animal body weight. This range has been determined to be acceptable, however is not believed to be limiting to the practice of the present method, and is merely presented herein in fulfillment of the duty to disclose a best mode for the practice of the invention. The present invention is therefore believed to encompass within its scope dosages lying outside the aforenoted range.

As mentioned earlier, certain testing was conducted in an effort to determine whether the redox agents proposed in accordance with the present invention would be effective in limiting the lethal effects of oxidant stress-inducing antibiotic compounds. Concomitantly, the effect of the redox dyes upon the antineoplastic activity of the antibiotics was also investigated. One of the parameters that was measured as described hereinafter, was the level and presence of glutathione (GSH), a low molecular weight compound known to be present in cardiac and hepatic tissues as a function NADPH presence and activity. Thus, reduced or depressed levels of glutathione would reflect a corresponding reduction in NADPH presence and activity, that would verify a competitive reaction with the redox agent.

Of the experiments that were conducted to verify the hypothesis underlying the present invention, the initial tests with laboratory mice as outlined below, failed to take into account the circadian rhythmicity of the toxicity of the antibiotic compound to the mice. As a result, the initial tests proved inconclusive and were discarded. A subsequent review of the literature revealed the criticality of this rhythmicity and the consequent need to strictly control the timing of antibiotic administration. Accordingly, subsequent testing reported herein and set forth below, was performed with regard to circadian rhythmicity, and provided results that were conclusive and relevant to the verification of the present invention.

Broadly, the following experiments involved the administration of the representative redox dye, methylene blue to mice under various conditions, while corresponding control animals were given placebo, such as saline solution. The in vivo activity of methylene blue alone was examined, as well as its in vivo activity in relation to the toxicity of the anthracycline antibiotic, doxorubicin. In this latter investigation, certain of the tests were performed with mice that had contracted leukemia from innoculation with a specifically chosen strain of leukemic cells, for the purpose of assessing the effect, if any, of the redox agent on the anti-neoplastic activity of the antibiotic.

The test procedures, materials and methods are set forth initially below, and the particular experiments follow.

EXPERIMENTAL MATERIALS AND METHODS

A. Animal Handling

Mice were obtained from Laboratory Supply Company, Inc., Indianapolis, Indiana. As discussed generally above, doxorubicin toxicity is known to exhibit a well known circadian rhythmicity with respect to all of its parameters; accordingly, the mice were housed and maintained on a standard lighting regimen of alternating periods of 12 hours of darkness and light. The light was maintained between 6:00 in the morning and 6:00 at night, and food and water were freely available. The rooms the mice were maintained in were sound insulated and kept at a constant relative humidity with a temperature ranging between 23° and 25° C. All animals were kept undisturbed except for a weekly cage cleaning, for 21 to 28 days after receipt from the animal supplier and prior to the experimentation. Four mice of the same sex were kept in each cage because of the well-known effects of isolation upon various biologic parameters. All experiments were performed upon the mice at between 2 and 4 hours after the lights were turned on, as this period, early in the reacting phase of the animal, had been previously demonstrated to be the most toxic circadian stage for doxorubicin adminstration. (See, Levi, F., Halberg, F., Haus, E., Sanchez, S., Sothern, R. B., Halberg, E., Hrushesky, W., Brown, H., Scheving, L. E., and Kennedy, B. J., "Synethetic Adrenocorticotropin for Optimizing Murine Circadian Chronotolerance for Adriamycin", *CHRONOBIOLOGIA*. 7(#2):227-244 (1980)).

B. Drugs

The anthracycline antibiotic doxorubicin (NDC 38242-874-10, obtained from Adria Laboratories, Inc., Columbus, Ohio) was prepared to a concentration of 2 mg/ml in saline immediately prior to administration to the mice. Administration was by injection either intravenously through a transilluminated tail vein or intraperitoneally. The doxorubicin was administered in an amount per body weight of mouse of 18 mg/kg. This particular dosage of doxorubicin, when administered intraperitoneally, conventionally kills more than 80% of $CD_2F_1$ and 100% of Balb/c female mice of virtually any age within 30 days. Intravenous administration also causes nearly 100% mortality in both strains, but the $CD_2F_1$ mice survived more than 3 times longer than the Balb/c mice.

Methylthionine chloride (methylene blue-MB; NDC 12894; obtained from United States Biochemical, of Cleveland, Ohio) was dissolved in sterile saline to a final concentration of 5 mg/ml. Methylene blue was administered to the mice either intravenously through a 27-gauge needle into a transilluminated tail vein subcutaneously on the back, or intraperitoneally. With respect to acceptable dosages, previous studies in mice, dogs and humans indicated that a methylene blue dosage of 25 mg/kg was well tolerated. Further screening performed pursuant to the present testing, determined that 100 mg/kg of methylene blue administered to mice 50% intravenously and 50% interperitoneally, did not kill $CD_2F_1$ female mice, while 550 mg/kg of methylene blue, 50 mg/kg of which was initially administered intravenously with the remainder administered intraperitoneally and subcutaneously, killed 50% of the same strain of mice. It was therefore decided for the purpose of the present experimentation to remain within the aforenoted range, and, preferably below the aforenoted lethal maximum.

C. Leukemic Cells

A strain of leukemia identified as L1210 was obtained from Arthur Bogden of the E. G. Mason Research Institute Animal and Human Tumor Bank, Worcester, Massachusetts. The tumor was kept in passage in DBA female mice. The tumor used for the below described experiments was between its tenth and twentieth in vivo passage. The chosen tumor proved to be extremely predictable in its behavior as, after intraperitoneal administration of 70,000 live tumor cells, for example, animals live 9.6±0.2 days, and after the administration 100,000 such cells, the animals survived 7.8+0.2 days. The tumor grows in ascites, which is initially clear and proceeds, within the 24 to 36 hours prior to death, to become hemorrhagic. Upon autopsy, the mice so innoculated also exhibit mesenteric and retroperitoneal adenopathy, however seldom exhibit parenchymal tissue invasion, and have no visible evidence of hematogenous metastatic tumor spread.

D. Cardiac Evaluation

A pathologist examined the heart of each mouse without prior knowledge of whether the animal received doxorubicin or placebo and methylene blue ur placebo. Cages were inspected twice daily for dead animals and autopsies were done immediately. The animals' hearts were washed in normal saline, fixed in formalin and embedded in glycol methacrylate. One-micron sections were inspected by light microscopy. The condition of the hearts was scored as follows: normal-1; slightly damaged-2; moderately damaged-3; severely damaged-4. Five specific categories or criteria were utilized for this evaluation: vacuolization; myofibrillar and nuclear degeneration; necrosis; interstitial edema; and interstitial inflammation. The numerical scores were averaged for each heart to yield an overall tabulation of damage.

E. Statistical Evaluation

T-tests were used when comparing variances between two groups. When the variance of means were compared among several groups, analysis of variance was used. Multivariate mean analysis was used when comparing groups of individuals sharing common characteristics which were anticipated might possibly affect the outcome of the statistical analysis. Front end variables considered in this multivariate survival analysis included strain, sex and age of the mouse; previous treatment (in one study); type of treatment (doxorubicin or placebo and methylene blue or placebo); as well as dose of each treatment. Chi-square analyses were used to compare survival percentages between and among various treatment groups at appropriate truncation points. Gehan-Wilcoxon Life Table Analyses were used to complement multivariate survival analyses in order to properly weight long-term survivors.

F. Glutathione Analysis

Total glutathione, oxidized and reduced (GSSG and GSH respectively), was determined by a modification of the method of Tietze (Tietze, F., *ANAL. BIOCHE.*, 27:502-522 (1969). GSH was determined by the method of Prins and Loos (Prins, H. K. and Loos, J. A., "In Biochemical Methods in Red Cell Genetics", J. Yunis, ed., Academic Press, New York, (1969)).

The following examples represent investigation of the chosen parameters in an effort to determine the efficacy of the method and redox agents of the present invention in decreasing the lethality of oxidant stress-inducing antibiotic administration, and particularly the effect of the upon NADPH concentrations and activities. Generally, the following tests utilized the materials and methods described in detail above and reference should be made thereto unless otherwise specified in the particular example.

EXAMPLE I

Effects of Methylene Blue on Tissue GSH

To determine whether methylene blue administration caused functional depletion of NADPH in vivo, levels of cardiac and hepatic GSH were monitored after methylene blue administration. Because maintenance of GSH is an NADPH-dependent process, decrements in intracellular NADPH were postulated to lead to a decrease in GSH concentration. To test this, 33 week old $CD_2F_1$ female mice were given 25 mg of methylene blue or saline intravenously, and were killed four hours thereafter, at which time GSH was immediately determined. Cardiac GSH levels were $6.96 \pm 1.24$ $\mu Mol/g$ of protein in the animals which received placebo (n=8), and $4.81 \pm 0.91$ p Mol/g of protein in mice given methylene blue (n=−9) (f=16.1, p<0.001). The results of this comparison are set forth in FIG. 1 herein. Hepatic GSH was similarly observed and noted to behave in corresponding fashion. Thus, the mean hepatic GSH levels in saline-treated animals were $15.03 \pm 4.33$ $\mu Mol/g$ protein (n=9) as compared to $9.30 \pm 5.50$ $\mu Mol/g$ protein (n=9) (f=6.03, p<0.03) in the group to which methylene blue was administered.

The results of this investigation confirm that methylene blue does interact with NADPH as postulated, and by lowering the level of the latter, could offer a means of effectively competing with, and thereby minimizing the interaction between anthracycline antibiotics and NADPH.

EXAMPLE II

Effects of Methylene Blue on Anthracycline Toxicity

A series of experiments were then conducted to determine whether methylene blue might protect against anthracycline-induced cardiotoxicity. In all studies, female mice of stated ages and strains were fed ad libitum and kept on the lighting regimen specified earlier, wherein the lights were maintained from 6:00 in the morning until 6:00 in the evening. Doxorubicin solutions prepared in accordance with the procedures explained earlier, were administered consistently at times ranging from 2 to 4 hours after the lights were turned on.

Study No. 1

Thirty-seven one year old Balb/c female mice were randomized to receive intravenous or intraperitoneal doxorubicin at weight concentrations of 18 mg/kg, or equal volumes of saline placebo, followed within five minutes by either methylene blue or saline placebo administered intravenously. All mice receiving only saline or saline and methylene blue lived throughout the study follow-up period. In this study, no significant effect of the particular route of administration of doxorubicin was observed by two-way analysis of variance. Therefore, the data were analyzed without regard to this variable.

More than 50% of the animals given doxorubicin alone were dead within 15 days, whereas at this time, all of those given both doxorubicin and methylene blue were still alive. Since no animals died between days 30 and 45, survival time at day 33 was analyzed by two-way anaysis of variance. Methylene blue was found to protect these mice from doxorubicin lethality regardless of the route of doxorubicin administration (f=10.4, p<0.003).

Gehan-Wilcoxon Life Table Analysis was also employed in order to properly consider the survival of animals still alive in each group (the group receiving methylene blue and the group not receiving methylene blue) at the time that the study was terminated. This analysis also revealed a very large survival advantage to mice who had received intravenous methylene blue immediately after doxorubicin whether administered intravenously or intraperitoneally (w score=−2.61, p<0.01).

In the course of this study, the cages were inspected twice daily for dead animals, and within twelve hours of death an autopsy was performed upon each animal that died. The heart was excised, inspected, washed in normal saline and fixed in 10% formalin. Upon terminatiun of this study, animals which had received no doxorubicin were killed by cervical dislocation and their hearts were handled in accordance with the procedures outlined earlier above. All hearts from animals not receiving doxorubicin appeared visually normal, while hearts from animals receiving doxorubicin were often pale and had a patchy fibrotic appearance. Pleural fluid, pulmonary consolidation and ascites were often present in animals which had received doxorubicin but never in animals killed after saline and/or methylene blue only.

A one-way analysis of variance of the mean heart damage score was then used to compare hearts from animals which received or did not receive methylene blue. The most prominent finding in the latter group was degeneration of myocytes. A higher (worse) heart damage score was seen in animals which did not receive methylene blue ($2.8 \pm 1.3$) as compared to those which did receive methylene blue ($1.8 \pm 0.9$) (normal score=1.0). Nonetheless, this difference in mean value was not statistically significant at the 5% level (f=2.3, p<0.1 and >0.05).

Study No. 2

Although the above study indicated that methylene blue diminished doxorubicin toxicity, the protection was by no means absolute. In an attempt to improve the effect of methylene blue, an additional study was conducted with $CD_2F_1$ mice which, as noted earlier, characteristically survived longer than Balb/c mice when given doxorubicin. These animals were also given more extensive and prolonged prophylaxis with methylene blue. A total of 15 $CD_2F_1$ female mice 12 to 14 weeks of age were randomized to receive 18 mg/kg of doxorubicin followed by either 4 injections each of 25 mg/kg of methylene blue or equal volumes of saline placebo. The first methylene blue or placebo injections were intravenous and were immediately followed by injection of doxorubicin. The next 3 injections of methylene blue, each in an amount of 25 mg/kg, were administered intraperitoneally at 1, 3 and 6 hours following the injection of doxorubicin.

As expected, the young $CD_2F_1$ female mice given doxorubicin alone lived three times longer than did Balb/c mice given the same dose of doxorubicin intravenously, as indicated in Study No. 1.

The present study was truncated for analysis at 130 days following doxorubicin administration, after the animals ceased dying. Mice receiving intravenous doxorubicin without methylene blue had a mean survival time of 85±7 days (n=7), while those animals receiving methylene blue after the administration of doxorubicin had an average survival of 113±0.5 days (n=8) (t=4.0, p<0.001). The foregoing results are graphically depicted in FIG. 2.

In addition, at this point 88% of the animals that received methylene blue were still alive, compared with only 28% of the mice who had been given placebo following the administration of doxorubicin ($\chi^2$=3.69, p<0.05), demonstrating near complete protection by administration of methylene blue. These results are graphically set forth in FIG. 3.

EXAMPLE III

In additional investigations, a total of 64 twelve to fourteen week old female Balb/c mice were studied for the effect of lesser doses of methylene blue on doxorubicin toxicity. Randomized mice were given 18 mg/kg doxorubicin either intravenously or intraperitoneally, 4 hours after lights on, followed immediately by either 25 mg/kg methylene blue by intravenous injection, or an equal volume of saline placebo.

All of the mice succumbed to doxorubicin regardless of route of administration. A 2-way analysis of variance of survival time at last death demonstrated an effect of methylene blue treatment; thus, animals which received methylene blue survived an average of 10.3±1 day, whereas, animals which received saline placebo survived an average of 7.2±0.6 days (f=10.8, p<0.001). There was also an effect of route of administration, in that intraperitoneally administered doxorubicin killed the mice much more quickly than doxorubicin that was administered intravenously; thus, animals receiving doxorubicin intraveneously survived an average of 11.2±0.6 days, while animals receiving doxorubicin intraperitoneally survived an average of 6.2±0.8 days (f=27.4, p<0.001). The Geha-Wilcoxon Life Table Analysis showed a substantial advantage for those mice which had received methylene blue, and intravenous doxorubicin (w=2.57, p<0.005).

EXAMPLE IV

Further tests were conducted to determine the effect of methylene blue on the anti-neoplastic activity of doxorubicin. As discussed earlier, if methylene blue were to protect neoplastic and normal cells alike against doxorubicin, this effect would have no clinical utility. Accordingly, it was determined to assess tne anti-tumor efficacy of doxorubicin administered with and without methylene blue. For these studies, 120, 12 to 14 week old female $CD_2F_1$ mice were each given 70,000 live L1210 leukemia cells 4 hours after the lights were turned on in the cages. The mice were then randomly assigned to one of seven treatment groups. These groups included a group which received placebo only, and others receiving 5 mg/kg, 18 mg/kg, or 36 mg/kg of doxorubicin at 4 hours after lights were turned on, followed by either placebo or methylene blue. The methylene blue was administered in an amount based on body weight of 25 mg/kg, and both methylene blue and placebo were administered by intravenous injection 30 minutes after doxorubicin, and further, subcutaneous injection at intervals of 1.5 hours, 4 hours, 12 hours, 24 hours and 48 hours later.

A two-way analysis of variance of means survival showed that this single doxorubicin treatment, administered 3 days after tumor implantation had a theraupeutic effect within an increased life span of 160% (F=124, p<0.001). Animals receiving doxorubicin and placebo lived 14.4±1.2 days while animals receiving doxorubicin followed by the administration of methylene blue lived 14.7±0.5 days. The foregoing results are graphically set forth in FIG. 4.

From the foregoing results, it should be apparent that the administration of methylene blue in conjunction with the administration of doxorubicin, offered the desired specificity that permitted doxorubicin to retain its anti-neoplastic efficacy. There was therefore no abatement in tumorous cell death. Rather, those groups of mice that received both doxorubicin and methylene blue exhibited improved survival rates, suggesting, in addition to unabated anti-neoplastic activity, that the cardiotoxicity attributable to doxorubicin was reduced.

In addition to the method set forth earlier and illustrated by the foregoing experiments, the present invention extends to suitable redox agents also enumerated earlier, that are capable of increasing animal tolerance to oxidant stress-inducing antibiotic compounds in the manner already described. These agents include the redox dyes listed herein, as well as other nontoxic redox compounds.

As mentioned earlier, the present method and associated redox agents are particularly noteworthy in that they are highly specific. As illustrated in the Examples, the redox agents are capable of interacting with NADPH or its reducing proteins, and thereby inhibiting the activity of the anthracycline compounds, in a way that would be expected to reduce the anti-neoplastic activity of these compounds as well. By contrast, the anti-neoplastic activity is shown to proceed unabated, as it is theorized, the redox agents are able to enter normal cells but do not make entry into the tumorous cells. Accordingly, in the tumorous cells the reaction between the anthracycline compounds and NADPH or its reducing proteins proceeds without inhibition, and these cells eventually die.

The present invention also includes a method for the treatment of cancer, comprising administering an anti-neoplastic compound, and within a clinically effective proximate time period, administering a non-toxic redox agent, the redox agent administered in an amount related to the amount of anti-neoplastic compound and further, that is effective to increase the tolerance of the animal under treatment to the reception of the anti-neoplastic compound.

More specifically, the present method comprises administering either concurrently or within a clinically effective period either before or after, a quantity of a redox agent in an amount sufficient to reduce the level of oxidant stress induced by the activity of the anti-neoplastic compound and imposed on the normal cells of the tissues of the animal adjacent to the situs of the tumorous cells under treatment. The redox agents and the method of their administration may correspond to those agents and techniques disclosed hereinabove.

This invention may be embodied in other forms or carried out in other ways without departing from the spirit or essential characteristics thereof. The present disclosure is therefore to be considered as in all respects illustrative and not restrictive, the scope of the inven-

What is claimed is:

1. A method for increasing animal tolerance to oxidant stress inducing antibiotics derived from a class of compounds selected from the group consisting of anthracycline compounds comprising administering to an animal in need of such treatment an effective amount of a nontoxic redox dye capable of depleting NAD(P)H levels in the animal, within a clinically effective period proximate to the time of administration of said antibiotic to said animal.

2. The method of claim 1 wherein said redox dye is administered in an amount from about 25 mg/kg to about 300 mg/kg of animal body weight.

3. The method of claim 1 wherein said redox dye is administered orally.

4. The method of claim 1 wherein said redox dye is administered parenterally.

5. The method of claim 4 wherein said redox dye is administered intraperitoneally.

6. The method of claim 4 wherein said redox dye is administered intraveneously and intraperitoneally.

7. The method of claim 4 wherein said redox dye is administered intraveneously.

8. The method of claim 4 wherein said redox dye is administered subcutaneously.

9. The method of claim 1 wherein said redox dye is administered prior to the administration of said antibiotic.

10. The method of claim 1 wherein said redox dye is administered concurrently with the administration of said antibiotic.

11. The method of claim 1 wherein said redox dye is administered after the passage of a clinically effective delay period following the commencement of administration of said antibiotic.

12. The method of claim 11 wherein said delay period extends to within 5 to 30 minutes after the commencement of the administration of said antibiotic.

13. The method of claim 1 wherein said redox agent is administered prior to and at least partially concurrently with the administration of said antibiotic.

14. The method of claim 1 wherein said redox dye also comprises a dye of the thiazine group.

15. The method of claim 1 wherein said redox dye is selected from the group consisting of dyes of the 52,000 Series of the Color Index.

16. The method of claim 15 wherein said redox dye comprises methylene blue.

17. The method of claim 16 wherein said anthracycline antibiotic comprises doxorubicin.

18. The method of claim 1 wherein said redox dye is selected from the group consisting of methylene blue, thionin, Azure A, Azure B, Azure C, methylene green, new methylene blue N, toluidine blue O and methylene green.

19. The method of claim 18 wherein said anthracycline antibiotic comprises doxorubicin.

20. The method of claim 1 wherein said anthracycline antibiotic is selected from the group consisting of daunorubicin, doxorubicin, Chromomycin A, olivomycin, Rhodomycin A and Rhodomycin B.

21. In a method of claim 1 wherein said method comprises a method for treating cancer in said animal wherein said oxidant stress inducing antibiotic possesses anti-neoplastic activity and is administered to the locus of the cancerous tissue of said animal the improvement comprising administering the non-toxic redox dye in conjunction with said anthracycline oxidant stress inducing antibiotic.

22. An antibiotic composition for administration to animals in need thereof comprising an oxidant stress-inducing anthracycline-derived antibiotic compound and an effective amount a nontoxic redox dye capable of depleting the NADP(H) levels in said animal and thereby increasing the tolerance of said animals to said antibiotic compound.

23. The composition of claim 22 wherein said redox dye comprises a thiazine dye.

24. The composition of claim 22 wherein said dye is selected from the group consisting of dyes of the 52000 Series of the Color Index.

25. The composition of claim 24, wherein said redox dye comprises methylene blue.

26. The composition of claim 25, wherein anthracycline antibiotic comprises doxorubicin.

27. The composition of claim 22 wherein said dye is selected from the group consisting of methylene blue, thionin, Azure A, Azure B, Azure C, methylene green, new methylene blue N, toluidine blue O, and mathylene violet.

28. The composition of claim 27 wherein said anthracycline antibiotic comprises doxorubicin.

29. The composition of claim 22, wherein said anthracycline antibiotic is selected from the group consisting of daunorubicin, doxorubicin, Chromomycin A, olivomycin, Rhodomycin A and Rhodomycin B.

* * * * *